(12) United States Patent
Siedenburg et al.

(10) Patent No.: US 12,089,985 B2
(45) Date of Patent: Sep. 17, 2024

(54) PATIENT MONITORING AND TREATMENT SYSTEMS AND METHODS

(71) Applicant: Stryker Corporation, Kalamazoo, MI (US)

(72) Inventors: Clinton T. Siedenburg, Everett, WA (US); Arthur T. Lounsbery, Woodinville, WA (US); Mitchell A. Smith, Sammamish, WA (US); Robert G. Walker, Seattle, WA (US)

(73) Assignee: Stryker Corporation, Portage, MI (US)

( * ) Notice: Subject to any disclaimer, the term of this patent is extended or adjusted under 35 U.S.C. 154(b) by 749 days.

(21) Appl. No.: 16/013,627

(22) Filed: Jun. 20, 2018

(65) Prior Publication Data

US 2018/0368804 A1    Dec. 27, 2018

Related U.S. Application Data

(60) Provisional application No. 62/524,088, filed on Jun. 23, 2017.

(51) Int. Cl.
*A61B 8/04* (2006.01)
*A61B 5/00* (2006.01)
(Continued)

(52) U.S. Cl.
CPC .............. *A61B 8/04* (2013.01); *A61B 5/0022* (2013.01); *A61B 5/0059* (2013.01);
(Continued)

(58) Field of Classification Search
CPC .... A61B 2560/0214; A61B 2560/0252; A61B 2562/242; A61B 5/0022; A61B 5/0059; A61B 5/0064; A61B 5/02007; A61B 5/02028; A61B 5/0205; A61B 5/02108; A61B 5/02125; A61B 5/0245; A61B 5/029; A61B 5/0452; A61B 5/0531; A61B 5/08; A61B 5/0836; A61B 5/14551; A61B 5/14552; A61B 5/6833; A61B 8/04; A61B 8/06; A61B 8/4236; A61B 8/4416;
(Continued)

(56) References Cited

U.S. PATENT DOCUMENTS 5,535,747 A    7/1996  Katakura
6,113,539 A *  9/2000  Ridenour ................. A61B 5/68
                                                   128/903
(Continued)

OTHER PUBLICATIONS

Office Action for U.S. Appl. No. 16/013,484, mailed on Aug. 17, 2020, Siedenburg, "Patient Monitoring and Treatment Systems and Methods," 11 pages.
(Continued)

*Primary Examiner* — Jonathan T Kuo
*Assistant Examiner* — Vynn V Huh
(74) *Attorney, Agent, or Firm* — Lee & Hayes, P.C.

(57) ABSTRACT

The disclosed non-invasive blood pressure systems and methods measure a patient's blood pressure without restricting blood flow. Other sensors, such as physiological sensors, sensors that sense data about the NIBP system components, and/or environment sensors sense data that is combined with the NIBP signal. The combined NIBP and sensor signals are used to measure a patient's non-invasive blood pressure.

20 Claims, 5 Drawing Sheets

(51) Int. Cl.

| | | |
|---|---|---|
| *A61B 5/02* | (2006.01) | |
| *A61B 5/0205* | (2006.01) | |
| *A61B 5/021* | (2006.01) | |
| *A61B 5/1455* | (2006.01) | |
| *A61B 5/349* | (2021.01) | |
| *A61B 8/00* | (2006.01) | |
| *A61B 8/08* | (2006.01) | |
| *A61H 31/00* | (2006.01) | |
| *A61B 5/0245* | (2006.01) | |
| *A61B 5/029* | (2006.01) | |
| *A61B 5/0531* | (2021.01) | |
| *A61B 5/08* | (2006.01) | |
| *A61B 5/083* | (2006.01) | |
| *A61B 8/06* | (2006.01) | |

(52) U.S. Cl.
CPC ........ *A61B 5/0064* (2013.01); *A61B 5/02028* (2013.01); *A61B 5/0205* (2013.01); *A61B 5/02108* (2013.01); *A61B 5/14551* (2013.01); *A61B 5/349* (2021.01); *A61B 5/6833* (2013.01); *A61B 8/4236* (2013.01); *A61B 8/5223* (2013.01); *A61H 31/005* (2013.01); *A61B 5/02007* (2013.01); *A61B 5/02125* (2013.01); *A61B 5/0245* (2013.01); *A61B 5/029* (2013.01); *A61B 5/0531* (2013.01); *A61B 5/08* (2013.01); *A61B 5/0836* (2013.01); *A61B 5/14552* (2013.01); *A61B 8/06* (2013.01); *A61B 8/4416* (2013.01); *A61B 8/488* (2013.01); *A61B 2560/0214* (2013.01); *A61B 2560/0252* (2013.01); *A61B 2562/242* (2013.01); *A61H 2201/165* (2013.01); *A61H 2201/168* (2013.01); *A61H 2201/5043* (2013.01); *A61H 2201/5058* (2013.01); *A61H 2201/5082* (2013.01); *A61H 2201/5084* (2013.01); *A61H 2201/5097* (2013.01); *A61H 2230/045* (2013.01); *A61H 2230/208* (2013.01); *A61H 2230/255* (2013.01); *A61H 2230/405* (2013.01)

(58) Field of Classification Search
CPC ............................. A61B 8/488; A61B 8/5223; A61H 2201/165; A61H 2201/168; A61H 2201/5043; A61H 2201/5058; A61H 2201/5082; A61H 2201/5084; A61H 2201/5097; A61H 2230/045; A61H 2230/208; A61H 2230/255; A61H 2230/405; A61H 31/005
USPC ............... 600/16–18, 300–301, 508–528
See application file for complete search history.

(56) References Cited

U.S. PATENT DOCUMENTS

| | | | |
|---|---|---|---|
| 2005/0228282 A1* | 10/2005 | Wang | G01S 7/52074 600/453 |
| 2006/0173514 A1* | 8/2006 | Biel | A61K 9/703 607/88 |
| 2006/0211942 A1 | 9/2006 | Hoctor et al. | |
| 2007/0010748 A1* | 1/2007 | Rauch | G16H 40/67 600/481 |
| 2008/0269818 A1 | 10/2008 | Sullivan et al. | |
| 2009/0117861 A1* | 5/2009 | Hoefel | H04B 1/385 600/300 |
| 2010/0022886 A1 | 1/2010 | Ayati et al. | |
| 2010/0030020 A1* | 2/2010 | Sanders | A61B 1/00105 600/109 |
| 2010/0176952 A1* | 7/2010 | Bajcsy | A61B 5/6887 340/573.1 |
| 2010/0217102 A1* | 8/2010 | LeBoeuf | G16H 50/20 600/310 |
| 2011/0009711 A1* | 1/2011 | Nanikashvili | A61B 5/0002 600/301 |
| 2011/0130669 A1* | 6/2011 | Garner | A61B 5/304 600/509 |
| 2015/0169835 A1* | 6/2015 | Hamdan | G16H 50/20 706/11 |
| 2016/0007862 A1* | 1/2016 | Ku | A61B 5/021 600/513 |
| 2016/0054354 A1* | 2/2016 | Keal | G01P 15/16 702/141 |
| 2016/0199251 A1 | 7/2016 | Aelen et al. | |
| 2016/0270673 A1 | 9/2016 | Aelen et al. | |
| 2017/0000688 A1 | 1/2017 | Kaufman et al. | |
| 2017/0209053 A1* | 7/2017 | Pantelopoulos | A61B 5/02125 |
| 2017/0231598 A1* | 8/2017 | Baek | A61B 8/54 600/454 |
| 2017/0354331 A1* | 12/2017 | Borkholder | A61B 5/02007 |
| 2018/0199834 A1 | 7/2018 | Siedenburg | |
| 2018/0206746 A1* | 7/2018 | Narasimhan | A61B 5/0225 |
| 2018/0235567 A1 | 8/2018 | Bezemer et al. | |
| 2021/0275131 A1 | 9/2021 | Siedenburg et al. | |

OTHER PUBLICATIONS

Office Action for U.S. Appl. No. 16/013,484, mailed on Nov. 14, 2019, Siedenburg, "Patient Monitoring and Treatment Systems and Methods", 9 pages.

Office Action for U.S. Appl. No. 16/013,484, mailed on Apr. 9, 2020, Siedenburg, "Patient Monitoring and Treatment Systems and Methods", 10 pages.

Office Action for U.S. Appl. No. 17/328,928, mailed on Sep. 7, 2023, Siedenburg, "Patient Monitoring and Treatment Systems and Methods", 8 pages.

* cited by examiner

PATIENT MONITORING AND TREATMENT SYSTEMS AND METHODS

CROSS-REFERENCE TO RELATED APPLICATIONS

This patent application claims the benefit of and priority to U.S. Provisional Patent Application Ser. No. 62/524,088, filed on Jun. 23, 2017, entitled "Noninvasive Blood Pressure (NIBP) Pulse Wave Velocity (PWV) by Ultrasound Sensor," the contents of which are hereby incorporated by reference in their entirety.

This patent application is related to concurrently filed U.S. patent application Ser. No. 16/013,484 entitled "PATIENT MONITORING AND TREATMENT SYSTEMS AND METHODS," the contents of which are hereby incorporated in their entirety.

BACKGROUND

Patient monitoring and treatment can involve invasive means that require inserting sensors within a patient to acquire the requisite data, such as a blood pressure of the patient. The blood pressure of a patient is a critical measurement that is used in monitoring and treating the patient. There are two means by which the blood pressure of the patient can be measured, one is invasive and the other is non-invasive. In the invasive means, the blood pressure is obtained by direct measurement, requiring a sensor to be inserted into the circulatory system of the patient to obtain the measurements. In certain situations that require precise, beat-to-beat blood pressure measurements, such as some surgical applications, the invasive means can provide the necessary data. Further, the invasive means can cause discomfort in the patient or the subject for which the blood pressure is being measured. Additionally, there is an increased risk of complications and/or increased expense due to the invasive nature of such blood pressure measurement.

In the non-invasive means, the sensing of the blood pressure is done externally to the patient and tends to only capture peak pressure readings, such as an intra-arterial blood pressure at diastole and systole, which provides little to no information about the patient's blood flow or vessel health. Typically, this involves the application of a cuff about a limb of the patient and the pressurization of the cuff to cut-off circulation through the limb. The pressure applied by the cuff to the limb is slowly reduced and as blood flow is resumed, the blood pressure can be measured based on the pressure remaining in the cuff. This process is often repeated multiple times to ensure an accurate measurement or as a means of monitoring over an extended period of time, with pauses required between measurement instances. While this means is non-invasive, it does require the temporary restriction of circulation in a portion of the patient, which can be damaging to the health of the patient and also requires time for the process to be fully performed. Additionally, such non-invasive blood pressure measurement techniques are sensitive to motion of the patient, accessories to the non-invasive blood pressure equipment being bumped or jostled during patient care or transport, etc., which can result in inaccurate and/or unobtainable blood pressure measurements. In patient transport or emergency situations, the patient and the equipment, such as the hosing, can be subjected to a large amount of motion during time in which an accurate blood pressure measurement can be critical to assess the state of the patient.

As such, there is a need for non-invasive patient monitoring and treatment systems and methods that can provide accurate patient information, such as blood pressure, for use in monitoring and/or treating the patient.

DETAILED DESCRIPTION

Non-invasive patient monitoring and treatment systems and methods are described herein. Non-invasive blood pressure (NIBP) measurement systems and/or methods can calculate a blood pressure and/or vessel dynamics of a person. Such data can be used in the monitoring and/or treatment of the person, such as for clinically evaluating a condition, or state, of the person. Additionally, the collected data can be correlated and/or aggregated with other physiological parameter data of the person. Correlated and/or NIBP data can provide indications of the effectiveness of a treatment of the person, can provide indications of potential changes in the clinical condition/state of the person and/or can provide data to assist with monitoring the clinical condition/state of the person.

The NIBP data can be collected with the assistance of an NIBP device. The NIBP device can radiate energy into tissues of the person. The radiated energy can reflect from one or more of the tissues, such as flowing blood, and the reflected energy can be detected, received, or sensed, by a sensor to generate an NIBP signal. The NIBP signal can be processed to calculate the blood pressure and/or vessel dynamics of the person. Additionally, the NIBP device can receive and/or process other physiological parameter data of the person to assist with monitoring and/or treatment of the person.

Figure 1:
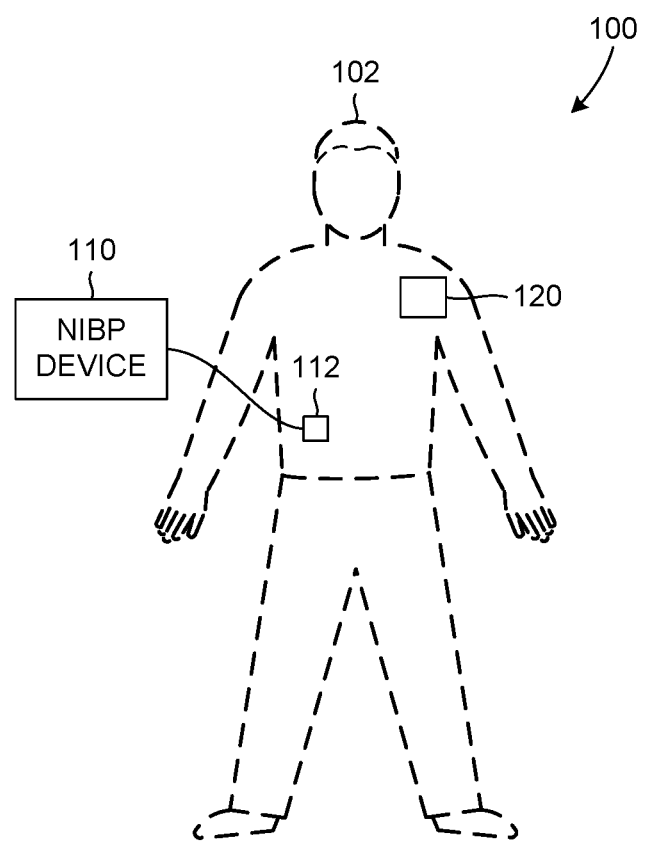
FIG. 1 is an example non-invasive blood pressure (NIBP) system.

FIG. 1 illustrates an example non-invasive blood pressure (NIBP) system 100. The NIBP system 100 can include an NIBP device 110 and an NIBP sensor 112 and/or an NIBP patch 120, which can be placed on a patient 102. The NIBP device 110 and sensor 112 and/or the NIBP patch 120 can determine a blood pressure and/or vessel dynamics, such as blood flow, size and/or position of a vessel, of the patient 102.

To calculate, or determine, the blood pressure and/or vessel dynamics of the patient 102, the NIBP sensor 112 and/or the NIBP patch 120 can radiate energy, such as ultrasound and/or light, into the tissues of the patient 102. The radiated energy will reflect from the various tissues, such as vessels, flowing blood, and/or other tissues/features, and the reflected energy can be sensed by the NIBP sensor 112 and/or the NIBP patch 120 to generate an NIBP signal, or data. The NIBP signal can be processed, such as by the NIBP device 110 and/or NIBP patch 120, to calculate a blood pressure and/or vessel dynamics of the patient 102.

Generally stated, the disclosed NIBP patch measures two values which can be used to compute a patient's instantaneous blood pressure. The NIBP patch measures the instantaneous non-invasive blood pressure (NIBP) of a patient with an apparatus that determines the values for, in one example, two of the unknowns in the water hammer equation: pulse wave velocity (PWV) and instantaneous blood velocity ($v_i$). The water hammer equation relates instantaneous blood pressure to pulse wave velocity and blood flow as follows:

$$P_i = \rho PWV v_i$$

where PWV is the pulse wave velocity, $\rho$ is the density of the blood which may be assumed to be a constant, for example, $v_i$ is the instantaneous velocity of the blood, and $P_i$ is the desired instantaneous blood pressure. Alternative equations relating the pulse wave velocity and blood flow can also be used.

Some conventional NIBP measurement systems rely on PWV to measure NIBP, but each requires an initial calibration measurement, taken at least once, to convert a relative blood pressure value to an actual blood pressure value. The required calibration measurement is typically taken using a traditional blood pressure cuff, for example on the patient's arm or perhaps the leg. Such conventional NIBP measurement systems that require an initial calibration and all calculations are based on a difference or differential value of that initial calibration measurement to achieve an actual measurement.

The disclosed NIBP systems and devices instead take an instantaneous blood pressure measurement rather than a change from an initial calibration measurement. Avoiding the need for a calibration measurement, prevents the patient from experiencing blood flow restriction altogether, which are required by all cuff-based NIBP systems. Although PWV is highly correlated with blood pressure (BP) so that changes in blood pressure can be calculated from changes in PWV by relying on an initial calibration measurement relatively accurately, the traditional calibration methods require use of a separate, initial calibration value or values to register a particular PWV to a particular value of blood pressure (as opposed to simply a change in blood pressure) for a patient. State of the art of NIBP using PWV typically uses a standard cuff-based measurement, to restrict the blood flow, in order to measure and associate a particular blood pressure to a particular PWV measurement in a patient. Restricting the blood flow requires that the patient's appendage being measured is compressed. Such restriction of the patient's blood flow prevents such conventional methods of measuring blood pressure from being applied to areas of the patient's body that cannot withstand restricted blood flow, such as a patient's neck, for example.

In this way, conventional methods and devices that provide NIBP measurements using PWV require a distinct calibration step. In contrast to the state of the art, the disclosed embodiments include a method and device that eliminate the requirement of a distinct calibration step, especially using a technology that temporarily restricts blood flow. In short, the disclosed embodiments include self-calibrating NIBP systems and methods using PWV, or alternatively, NIBP systems and methods using PWV without the temporary restriction of blood flow.

The lack of need for a calibration step for devices using the method taught herein arises by making an additional measurement of the vasculature such as blood velocity and a suitable equation such as the water hammer equation in its integrated (non-differential) form. In the water hammer equation, the blood pressure is related to the PWV by two scale factors—blood velocity and blood density—that can be known without a distinct calibration step. The scale factors are found using the same ultrasound technology that is used to measure the PWV. Blood velocity is measured according to the disclosure and blood density is assumed based on a known value with or without a correction factor. In this way, a particular blood pressure is calculated as the PWV scaled by the blood density and the blood velocity.

Blood velocity can be acquired using ultrasound as a time varying waveform. PWV can also be measured with ultrasound as a time varying function. The time-varying nature of the PWV means that it can be updated from beat to beat, if desired. The time-varying nature of the blood velocity means that blood velocity can be measured at a much finer resolution than at peak systole and diastole values during a cardiac cycle. Instead, the blood velocity is measured continuously throughout the duration of the cardiac cycle for as many cardiac cycles as desired. Because blood density is already sufficiently known and is relatively constant, not only can a particular blood pressure measurement be known from the scaling value of the PWV as if it were obtained by a standard cuff-based measurement or even an invasive catheter measurement, but all manners of blood pressure measurements can be made as time-varying waveforms describing the instantaneous pressure at as many points during a cardiac cycle as desired. Blood pressure can be monitored continuously throughout the cardiac cycle with as fine a resolution as is required, and this can be done for as many consecutive or periodic cardiac cycles as is desired for beat-to-beat monitoring, or as intermittently as desired.

Measuring the instantaneous blood pressure instead of its change relative to a calibrated baseline measurement means, for example, that as arterial walls stiffen (due to disease, drug therapy, and/or normal vasculature responses, for example) which increases the PWV, this new PWV value is measured along with any corresponding change in blood velocity to produce an updated blood pressure waveform. Additionally, if the heart pumps more or less energetically, the blood velocity changes accordingly, which results in the blood pressure changing proportionately, all else equal. This updated blood velocity measurement at the prevailing PWV (which characterizes the state of the vasculature) corresponds to the updated blood pressure after being scaled by blood density. In other words, since there are two measurements made, PWV and blood velocity, and not just PWV alone, a distinct calibration step is not needed, as the ambiguity of PWV by itself is remedied by adding the second measured value of blood velocity. This is of great value over conventional patient NIBP monitoring using PWV alone where typically the calibration step requires a blood pressure measurement performed by restricting blood flow, which can be more costly, time consuming, and/or uncomfortable to the patient. Ultrasound or light technology can be used to acquire both the PWV and the blood velocity although other methods of obtaining the PWV and the blood velocity can alternatively or additionally be used. Further embodiments implement various techniques and devices to measure or detect both pulse wave velocity and instantaneous blood velocity.

An NIBP sensor can be attached to a patient. As discussed at length above, the sensor includes an ultrasound sensor and may include one or more alternative sensors.

The NIBP sensor substantially simultaneously measures pulse wave velocity and instantaneous blood velocity, as discussed above. Each of those two basic steps may be accomplished in numerous ways. For example, pulse wave velocity may be measured using a sound analysis based on information known about the configuration of the NIBP sensor. In one specific embodiment, the sensor is configured such that an ultrasound waveform radiated by the sensor produces grating lobes having known characteristics, such as a grating lobe separation angle of θ. The sound analysis may further compute a depth from the sensor to a target blood vessel. Based on those data, ultrasound imaging combined with triangulation techniques can be used to compute a rate at which a pulse travels through the vessel, which is the pulse wave velocity of the vessel.

Similarly, instantaneous blood velocity may be measured using Doppler effect techniques. In one specific embodiment, the Doppler analysis can identify the phase change of a returned signal from the blood between each of 10 kHz repetitions, for example.

Once pulse wave velocity and instantaneous blood velocity are known, the instantaneous blood pressure is calculated by using an equation that relates the blood velocity to the PWV, such as the water hammer equation. Based on that equation, pulse wave velocity, instantaneous blood velocity, and blood pressure are related as follows:

$$P_i = \rho PWV v_i$$

Once calculated, the blood pressure measurement may be presented to a user for use in treatment of the patient. It should be appreciated that, in another alternative, continuous wave Doppler (CWD) may be used as an alternative to pulse wave Doppler (PWD).

The calculated blood pressure and/or vessel dynamics of the patient 102 can assist with monitoring and/or treating the patient 102. For example, the blood pressure and/or vessel dynamics data can be collected over an extended period of time to assist with monitoring the patient 102 and/or the efficacy of patient 102 treatment can be assessed based on the calculated blood pressure and/or vessel dynamics. Using such data, a user, device and/or system can alter treatment of the patient 102 to increase the efficacy of the administered treatment, such as cardiopulmonary resuscitation (CPR).

Data from the NIBP sensor 112, such as the NIBP signal/data, can be transmitted to the NIBP device 110 for processing. Communications between the NIBP device 110 and the NIBP sensor 112 can be via a wired and/or a wireless connection. In addition to communication, the connection between the NIBP device 110 and the NIBP sensor 112 can provide power from one or more of the NIBP device 110 and/or the NIBP sensor 112 to the other. The NIBP device 110 can display and/or transmit the blood pressure and/or vessel dynamics data to a user, device and/or system.

The NIBP patch 120 can be placed on and/or affixed to the skin of the patient 102, such as by an adhesive backing. With the NIBP patch 120 placed on and/or affixed to the patient 102, the NIBP patch 120 can calculate/monitor the blood pressure and/or vessel dynamics of the patient 102 in a continuous and/or interval manner. The NIBP patch 120 can remain on and/or affixed to the patient 102 for extended period times to allow the NIBP patch 120 to capture blood pressure and/or vessel dynamic data over the extended period of time.

Data, such as blood pressure and/or vessel dynamics, can be transmitted from the NIBP patch 120 to an external device and/or system. Such communication can be via a wired and/or a wireless connection, such as via a near-field communication (NFC), Wi-Fi Direct®, WiGig, cellular, and/or Bluetooth® connection. Additionally, or alternatively, the blood pressure and/or vessel dynamics data can be stored on the NIBP patch 120 for later retrieval.

Figure 2:
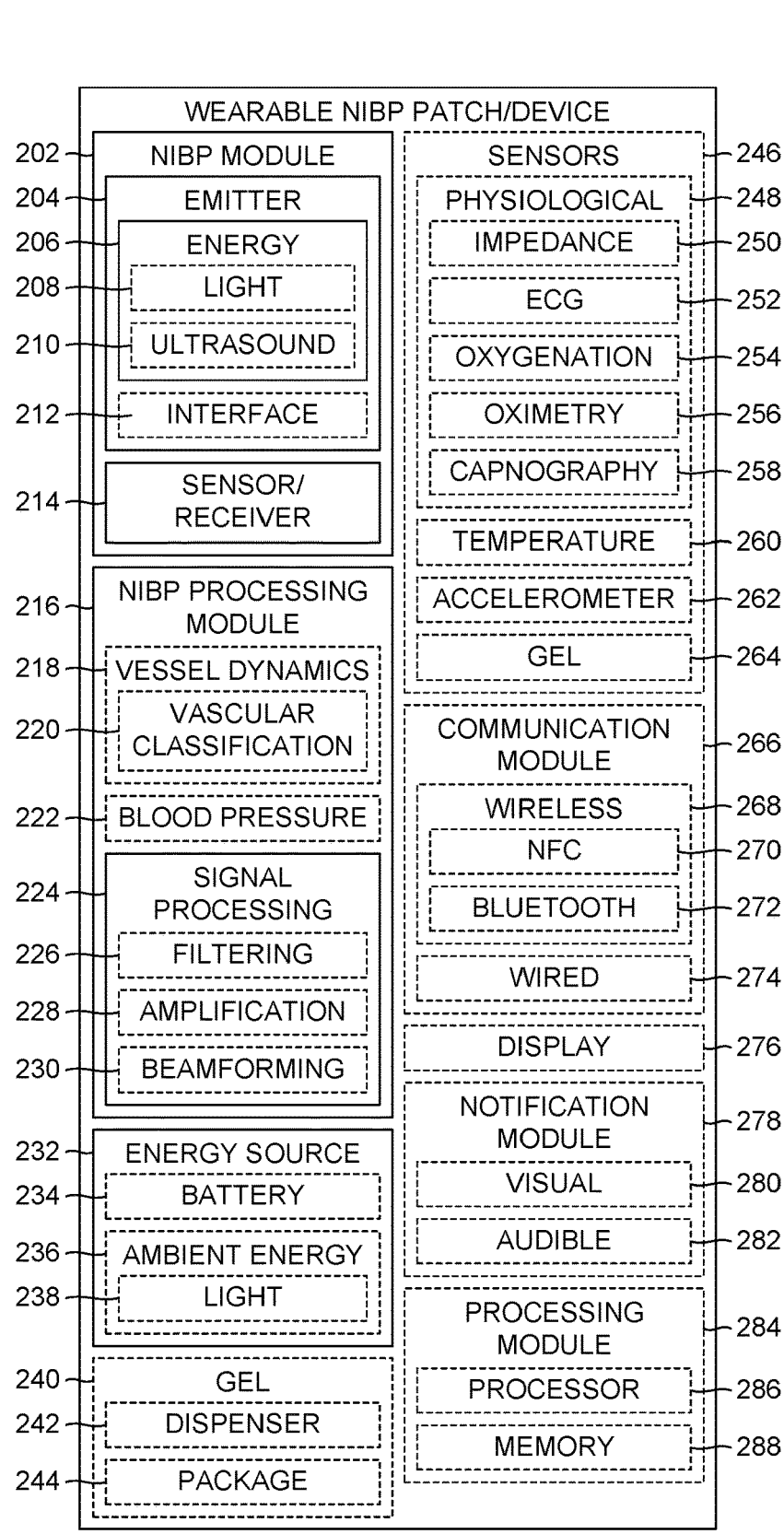
FIG. 2 is a block diagram of an example wearable NIBP patch or device.

FIG. 2 illustrates an example non-invasive blood pressure (NIBP) patch/wearable device 200 that can be placed on, or affixed to, a patient to determine/calculate a blood pressure and/or vessel dynamics of the patient. The NIBP patch/wearable device 200 can include various elements/systems, features and/or functionality that can be contained in/on the NIBP patch/wearable device 200. Example elements/systems, features and/or functionality of the NIBP patch/wearable device 200 can include an NIBP module 202, an NIBP processing module 216, an energy source 232, gel 240, sensor(s) 246, a communication module 266, a display 276, a notification module 278 and/or a processing module 284. Alternatively, one or more elements/systems, features and/or functionality of the NIBP patch/wearable device 200 can be distributed on, and/or integrated with, an external device/system.

The NIBP module 202 can include an emitter 204 and a sensor/receiver 214. The emitter 204 can radiate energy 206, such as light 208 and/or ultrasound 210, into tissues of a patient and the sensor/receiver 214 can receive energy reflected from the tissues of the patient. Reception of the reflected energy can cause the sensor/receiver 214 to generate an NIBP signal/data that can be processed to calculate a blood pressure and/or vessel dynamics of the patient.

An optional interface 212 of emitter 204 can assist with directing energy 206 of the emitter 204 into the patient's tissues. For ultrasound energy 210 radiation, the interface 212 can be textured with microstructures that can abrade the outer skin of the patient such that the microstructures of the interface 212 are acoustically integrated with the outer skin of the patient. This integration of the interface 212 and the patient's skin can direct the ultrasound energy 210 into the tissues of the patient without requiring the use of a gel.

The NIBP processing module 216 can receive the NIBP signal and/or data from the NIBP module 202 for processing 224 to calculate vessel dynamics 218 and/or blood pressure 222 of the patient. Processing 224 of the NIBP signal/data can include analog filtering 226, amplification 228 and/or beamforming 230. Beamforming 230 can be applied to, and/or implemented with, the ultrasound 210 emissions by the emitter 204 to assist with enhancing the ultrasound signal(s)/data captured by the sensor/receiver 214. The beamforming 230 can include controlling, or altering, the emission of the ultrasonic 210 emissions by the emitter 204, such as altering a phase and/or amplitude of the output ultrasonic energy 210.

Calculating vessel dynamics 218 can include calculating/determining a depth of a vessel, a cross-sectional area of the vessel, a flow rate through the vessel and/or other dynamics/characteristics of one or more vessels based on the NIBP signal/data. Based on the vessel dynamics 218, the NIBP processing module 216 can also classify 220 one or more of the vessels interrogated by the NIBP module 202. The vascular classification 220 can include classifying the one or more vessels as a vein or artery, such as based on a calculated flow velocity and/or pressure within the one or more vessels.

The on-board energy source 232 can provide power, such as electrical power, to the various elements, features and/or functions of the wearable NIBP patch/device 200. An example on-board energy source 232 can include a battery 234 and/or an ambient energy 236 capture/storage element, device, and/or system. The battery 234 can be a permanent or replaceable battery that can be placed on/in, or affixed to, the wearable NIBP patch/device 200. The ambient energy 236 capture/storage can harvest ambient energy from about the wearable NIBP patch/device 200, such as from light 238, heat, movement and/or radio transmissions/waves. The ambient energy 236 capture/storage can receive, or be exposed to, the ambient energy and can convert the received ambient energy into electrical energy that can be stored, such as in the battery 234. The ambient energy 236 capture can include a solar/photovoltaic cell, a thermoelectric element, a piezoelectric material, a generator, a magnet in motion relative to a coil, and/or an antenna, to harvest/capture ambient energy.

Prior to use, the energy source 232 can be isolated, such as by a removable material, from connecting to the NIBP patch/device 200 circuitry, elements, and/or systems. This isolation can assist with reducing, or minimizing, depletion of the energy source 232 when the NIBP patch/device 200 is not in use, such as during storage prior to use. To activate and/or prepare the NIBP patch/device 200 for use, a user can remove the isolation material, such as via a pull tab, to allow/electrically connect the energy source 232 to the circuitry of the NIBP patch/device 200.

Gel 240 can be included on and/or in the wearable NIBP patch/device 200 as a dispenser 242 and/or a package 244. The gel 240 can interface between the skin of the patient and an ultrasound 210 emitter 204 to assist with directing the ultrasound energy 210 into the tissues of the patient. The gel 240 can prevent an air space/separation between the skin of the patient and the emitter 204 to prevent the reflection of the ultrasound energy 210 from the surface of the patient's skin.

The dispenser 242 of gel 240 can be an element, device and/or system that can dispense the gel 240 below the emitter 204 prior to and/or during use of the emitter 204 and/or wearable NIBP patch/device 200. In an example, the wearable NIBP patch/device 200 can be worn for an extended period of time and during the time the NIBP patch/device 200 is worn by the patient, the dispenser 242 can dispense gel 240 continuously, at intervals, and/or as needed, for example by evaluating the image generated. The dispenser 242 can maintain a gel 240 interface between the patient's skin and the emitter 204 while the wearable patch/device 200 is affixed and/or collecting data.

The package 244 of gel 240 can be a self-contained package 244 of gel 240 that can be broken prior to, or as/due to, the wearable NIBP patch/device 200 is being affixed/attached to, and/or placed on, the skin of a patient. The package 244 can be positioned such that the gel 240 is deposited on and/or below the emitter 204 such that a gel 240 interface between the emitter 204 and the patient's skin is formed. In a disposable wearable NIBP patch/device 200, the package 244 of gel 240 can be affixed to the wearable NIBP patch/device 200. In an example, the package 244 of gel 240 can be integrated with the energy source 232 isolator, such that removal of the isolator causes the package 244 to break and dispense gel 240 and/or causes the package 244 to be exposed in a manner to allow breakage of the package 244 and the dispensing of gel 240 therefrom. In a non-disposable wearable NIBP patch/device 200, the package 244 of gel 240 can be manually placed, and/or broken, beneath the wearable NIBP patch/device 200 to form the gel 240 interface. Alternatively, gel 240 can be manually placed beneath the wearable NIBP patch/device 200 prior to attaching/placing the wearable NIBP patch/device 200 on the patient's skin.

The sensor(s) 246 of the wearable NIBP patch/device 200 can include a physiological sensor 248, a temperature sensor 260, an accelerometer 262, a gel sensor 264 and/or other sensors. The sensor(s) 246 can be placed on/in the wearable NIBP patch/device 200 to collect various sensor data of the patient, wearable NIBP patch/device 200, the ambient environment and/or other data. Alternatively, the sensor(s) 246 can be external to the wearable NIBP patch/device 200 and can communicate the sensed data via a wired and/or a wireless connection to the wearable NIBP patch/device 200. The data collected by the sensor(s) 246 can be transmitted from the wearable NIBP patch/device 200 to an external user, device and/or system and/or the data can be used with/in one or more functions and/or features of the wearable NIBP patch/device 200.

The wearable NIBP patch/device can include biocompatible materials, especially when intended for long-term contact with the patient's body. For example, the adhesive used to affix the NIBP patch/device to the patient could include similar adhesives found in conventional bandages and the patch material itself could also borrow from biocompatible materials used in typical bandages such as medical grade fabrics to avoid skin irritation. The gel used to wet the interface between an ultrasound NIBP patch/device and the patient's skin would also need to be biocompatible as would the sensor interface that contacts the patient's skin in the NIBP patch/device using any energy source (e.g., ultrasound and/or light). Still further, the ultrasound NIBP patch/device example would also include a biocompatible scan head lens(s), such as RTV, Rexolite, and/or some polyurethanes.

The physiological sensor(s) 248 can include an impedance sensor 250, an electrocardiogram (ECG) sensor 252, an oxygenation sensor 254, an oximetry sensor 256, a capnography sensor 258 and/or other physiological sensor 248. The collected physiological parameter data from the physiological sensor(s) 248 can be used by the wearable NIBP patch/device 200 to assist with monitoring and/or treatment of the patient to which the NIBP patch/device 200 is placed and/or affixed. Data from the sensor(s) 248 can be collected in a continuous and/or interval manner and can also be triggered by one or more events, such as a sensed value by the sensor(s) 246, a time and/or other trigger. Additionally, the physiological parameter data can be merged/processed with the blood pressure 222 and/or vessel dynamics 218 data to assist with monitoring and/or treatment of the patient. The merging/processing of such data can be performed on the wearable NIBP patch/device 200, such as by the processing module 284 and/or the NIBP processing module 216, and/or can be performed at/on an external device/system.

The temperature sensor 260 can monitor a temperature of the wearable NIBP patch/device 200 and/or the skin of the patient. In an example, the temperature sensor 260 can cause a performance parameter of the NIBP patch/device 200, such as a duty-cycle or sampling rate, of the wearable NIBP patch/device 200 to be decreased when a sensed temperature exceeds a threshold value which can prevent thermal damage to the patient's skin and/or patient discomfort while wearing the NIBP patch/device 200. Alternatively, or additionally, the temperature sensor 260 can cause one or more elements, devices and/or systems of the NIBP patch/device 200 to be disabled, such as temporarily, in response to a sensed temperature exceeding a value. Once the temperature sensor 260 senses that the temperature of the NIBP patch/device 200 and/or the patient's skin has decreased below a threshold, or other, value, the temperature sensor 260 can cause the NIBP patch/device 200 to resume normal, or prior, functioning.

The accelerometer 262 can sense motion of the NIBP patch/device 200. The accelerometer 262 can the NIBP patch/device 200 to monitor the motion, posture, position, acceleration and/or other motion parameters of the patient wearing the NIBP patch/device 200. In an example, the accelerometer 262 can trigger an alert/notification in response to one or more values, such as those that can indicate a collapse of the patient wearing the NIBP patch/device 200. Additionally, the accelerometer 262 can cause the acquisition of data, such as by the NIBP module 202 and/or sensors 246 in response to one or more values. In the example of a patient collapse, the NIBP module 202 can be triggered to acquire a blood pressure 222 and/or vessel dynamics 218 data to determine if the collapse was caused by, and/or caused, a physiological change of the patient.

Further, the accelerometer 262 can be integrated with another sensor, such as global positioning (GPS), and/or other geolocation, sensor which can determine a location of the patient wearing the NIBP patch/device 200. The location of the patient can be transmitted, such as by the communication module 266, to an external user, device and/or system in response to an accelerometer 262 value and/or change in value, such as caused by a collapse of the patient. Other data, such as sensor(s) 246 and/or NIBP module 202 data, can be transmitted along with the location of the patient.

The gel sensor 264 can monitor the integrity of the gel 240, such as a hydration of the gel 240. In extended period of wearing of the NIBP patch/device 200, the integrity of the gel 240 interface can deteriorate. The gel sensor 264 can monitor the integrity of the gel 240 interface and can trigger an alert, such as to apply more/new gel 240, and/or cause a dispenser 242 to dispense more gel 240 to the interface.

The communication module 266 can provide wired 274 and/or wireless 268 communications from and/or to the NIBP patch/device 200. The wireless communication 268 can be via a network, such as a Wi-Fi connection, Wi-Fi Direct, WiGig, cellular and/or can be a local connection, such as via near-field communication (NFC) 270 and/or Bluetooth® connection. Additionally, the NFC connection 270 can receive radio transmissions that can be converted to electrical power to provide power to one or more functions of the NIBP patch/device 200. Data transmission to and/or from the NIBP patch/device 200 can be with an external user, device and/or system and can include the various physiological data, such as sensor(s) 246 data and/or NIBP module 202 data, and/or instructions to cause the NIBP patch/device 200 and/or an external device/system to perform one or more functions.

Functioning/status of the NIBP patch/device 200 can also be obtained via the communication module 266. The NIBP patch/device 200 can be interrogated, such as via the NFC 270 and/or Bluetooth® 272 connection, for a status of the NIBP patch/device 200 and/or the status various elements, devices, systems and/or functionality thereof. As part of the interrogation, the NIBP patch/device 200 can also transmit identifying information, such as a serial number of the NIBP patch/device 200. Status of the NIBP patch/device 200 can include self-test data, a status of the gel 240 as sensed/determined by the gel sensor 264, an activation date of the NIBP patch/device 200, and/or other NIBP patch/device 200 status information. In an example, the status of the NIBP patch/device 200 can include a status of the energy source 232, remaining energy, remaining NIBP patch/device 200 run time on the available energy, and/or other status information regarding the energy source 232.

If the status of the NIBP patch/device 200 indicates a depleted and/or low power of the energy source 232, a user or other can replace the energy source 232 and/or replace the NIBP patch/device 200 with a new NIBP patch/device 200. As part of replacement of the NIBP patch/device 200, data from each NIBP patch/device 200 can be collected prior to removal of the old/depleted NIBP patch/device 200 to allow the measurements, such as blood pressure 222, to be compared for correlation. The correlation of the data can be used to verify that the data from each of the NIBP patches/devices 200 is correct, or agreed upon, between the two NIBP patches/devices 200. Alternatively, or additionally, the data collected from one or more of the NIBP patches/devices 200 can be corrected to align the data collected from both NIBP patches/devices 200.

An optional display 276 can provide a visual output to the user and/or others, such as to display the NIBP module 202, sensor(s) 246 and/or other data. The display 276 can include a screen upon which such data can be displayed and/or one or more other types of output to a user such as audible, visual, haptic, and/or other output. Additionally, the display 276 can provide input functionality, such as a touchscreen, to allow a user, or other, to input instructions and/or data to the NIBP patch/device 200.

The notification module 278 can provide visual 280 and/or audible 282 notifications, such as alerts, to the patient, a user, a device and/or system. Other types of notifications, such as haptic output, can also be used and any combination of the disclosed notifications can also be included. The notifications can be in response to sensed data, such as the blood pressure 222, vessel dynamics 218, sensor(s) 246 and/or other data. Additionally, and/or alternatively, the notifications can be with regards to one or more elements, devices and/or systems of the NIBP patch/device 200 and/or functioning thereof. For example, the notification module 278 can provide a notification when the energy source 232 is low so that a user can take appropriate action to continue the functioning of the NIBP patch/device 200, if desired/required.

When the energy source 232 is low, the user can be alerted to measure the battery consumption with a coulomb counter or alternatively an energy consumption estimator, for example. If blood pressure is still needed when the NIBP patch energy source is nearly drained, the user is alerted by the monitoring device. The user is prompted to place a new patch in place of or near the depleted one and measurements may be initially compared, in some examples, between the two NIBP patches before the near-depleted one is removed, and logged for any retrospective questions regarding differences in device or location on the body.

The processing module 284 can process data and/or control one or more functions/features of the NIBP patch/device 200. The processing module 284 can include a processor 286 and/or memory 288 for storing data and/or instructions for execution by the processor 286. Data stored in the memory 288 can include blood pressure 222, vessel dynamics 218, sensor(s) 246 and/or other data of the NIBP patch/device 200. The processing module 284 can monitor/process data from the sensor(s) 246 and/or the NIBP module 202 and can cause one or more function/features of the NIBP patch/device 200 to be performed in response to the data. Additionally, the processing module 284 can receive data and/or instructions from an external device/system, such as via the communication module 266, and can cause one or more function/features of the NIBP patch/device 200 to be performed in response.

The processing module 284 can also control the acquisition of data, such an NIBP signal/data and/or sensor(s) 246 data, by the NIBP patch/device 200. The processing module 284 can schedule the data acquisition, such as a continuous, interval and/or spaced apart data acquisition(s). Further, the acquisition of data via the NIBP module 202, NIBP processing module 216 and/or the sensor(s) 246 can be combined or interleaved, such as based on a desired, or required, sampling rate for the one or more data acquisitions. Alternatively, the acquisition of the NIBP data and/or sensor data can be asynchoronously combined. Additionally, the acquisition of data by the NIBP patch/device 200 can be performed on an instructed basis, such as in response to receiving an external communication via the communication module 266 to cause one or more of a blood pressure 222, vessel dynamics 218, and/or sensor(s) 246 data.

Figure 3:
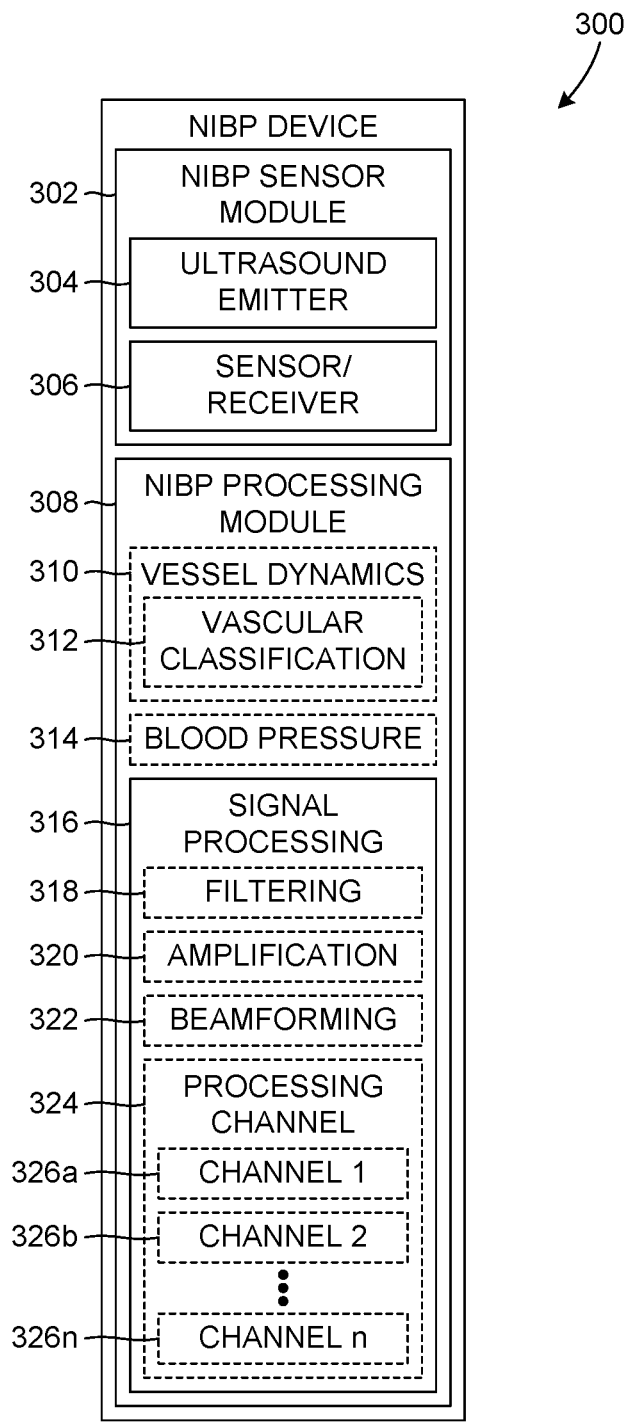
FIG. 3 is a block diagram of an example NIBP device.

FIG. 3 illustrates an example non-invasive blood pressure (NIBP) device 300 that can calculate, or determine, one or more vessel dynamics 310 and/or blood pressure 314 of a patient that the NIBP device 300 monitors, as discussed above. The NIBP device 300 includes an NIBP sensor module 302 and an NIBP processing module 308. The NIBP sensor module 302 can radiate energy into tissues of the patient and can sense, or receive, energy reflected therefrom to generate an NIBP signal and/or data. The NIBP processing module can process the NIBP signal/data to calculate the blood pressure 314 and/or vessel dynamics 310 of the patient.

The NIBP sensor module 302 can include an ultrasound emitter 304 and a sensor/receiver 306. The ultrasound emitter 304 radiates ultrasound waves into the tissues of the patient and the reflected energy can be sensed by the sensor/receiver 306 to generate the NIBP signal/data.

The NIBP processing module 308 can include signal processing 316 to calculate the blood pressure 314 and/or vessel dynamics 310 of the patient based on the NIBP signal and/or data from the NIBP sensor module 302. The signal processing 316 can include filtering 318, amplification 320 and/or beamforming 322. The NIBP signal/data can be received at the NIBP processing module 308 via various processing channels 324, such as channel 326a, 326b . . . 326n. The number of processing channels 324 can be based on a sampling rate, and/or number of sensors, of the sensor/receiver 306 of the NIBP sensor module 302, and/or other sensors, such as physiological sensors, that can be included on and/or communicate with the NIBP device 300. A typical ultrasound machine is used to image internal structures of the patient, in comparison, the ultrasound of the NIBP device 300 is used to generate data from which various parameters can be calculated. Due to the simplified nature, the number of processing channels 324 required in the NIBP device 300 can be significantly lower, or fewer, than the number of processing channels of a typical ultrasound imaging device. The number of processing channels 324 of the NIBP device 300 can be sufficient enough to allow for multiple sensors of the sensor/receiver 306 to generate NIBP signal(s)/data for processing. The number of sensors of the sensor/receiver 324 can allow for a wide area of patient tissue from which NIBP signal/data can be gathered/received. The processing of the NIBP signal/data can focus on a target vessel(s) based on the NIBP signal/data. To focus the ultrasound emitter 304 on the target vessel(s), the beamforming 322 can be used to direct the emitted ultrasound.

Figure 4:
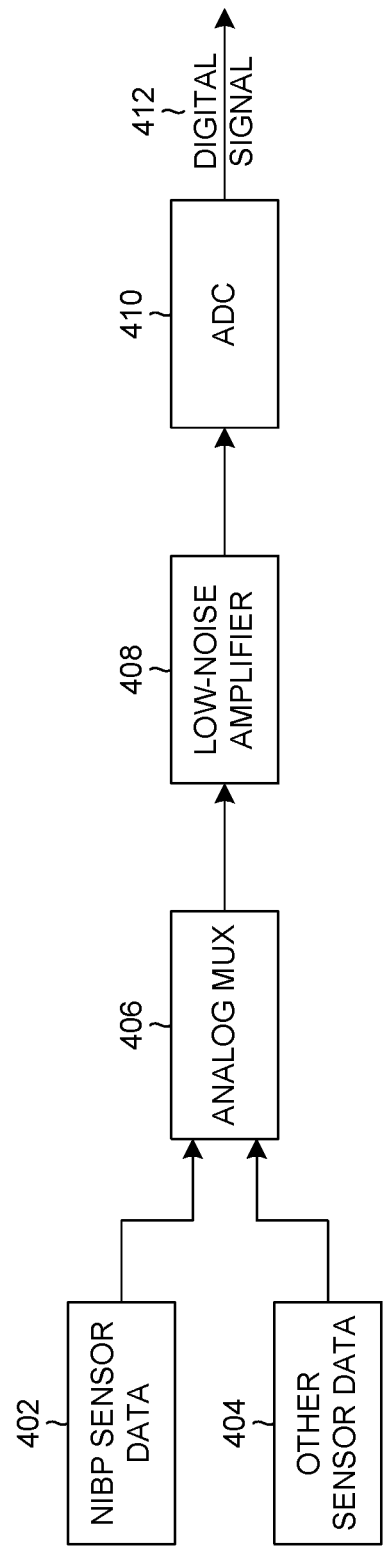
FIG. 4 is a block diagram of an example signal processing system.

The signal processing 316 can include an analog-to-digital converter (ADC), such as 410 of FIG. 4, to convert the reflected ultrasound energy, received by the sensor/receiver 306, into a digital signal 412. The sampling rate of the ADC 410 can be relatively high, allowing the interleaving of sampling of other sensors, such as other physiological sensors. In this manner, a single ADC 410 can be used in the sampling of not only the NIBP signal/data 402, but also data 404 from other sensors of, and/or communicating with, the NIBP device 300. The other sensors can require reduced sampling rates in comparison to the sampling rate of the sensor/receiver 306 and so can be combined or interleaved. An analog multiplexer (MUX) 406 can be connected to the input of the ADC 410 to combine the multiple inputs. The MUX can include any semiconductor switch, such as a metal-oxide semiconductor field-effect transistor (MOSFET) switch for example, or a microelectromechanical systems (MEMS) switch.

Certain sensors, such as ECG sensors, can require higher sampling rates compared to other sensors, in which case the sampling rate and/or interleaving of the ADC 410 can be adjusted/modified to allow the NIBP signal/data 402 and/or other sensor data 404 to be sampled as needed/required. Further, a low-noise amplifier (LNA) 408 can be disposed between the MUX 406 and the ADC 410, allowing the multiple sensors, such as those of the sensor/receiver 306, to share a single LNA 408, which can reduce cost and/or complexity of the NIBP device 300. Alternatively, the MUX can be disposed between the LNA and the ADC if signal amplification is needed before entering the MUX. Additionally, multiple LNAs can be used that are each disposed to condition the signals that are input to a single MUX in some examples.

Beamforming 322 and/or other imaging techniques can be used to assist with collecting/generating the NIBP signal and/or data. Example beamforming techniques can include synthetic aperture imaging, plane-wave imaging, very fast Doppler imaging, adaptive beamforming, panoramic imaging and/or other beamforming techniques. Example other imaging techniques can include isonification techniques, such as harmonic imaging, coded pulses and/or FM pulses, and/or other signal/image processing techniques, such as compression, segmentation, pattern recognition, classification, and/or other techniques. Using the beamforming 322 and/or other imaging techniques, the NIBP sensor module 302 and/or the NIBP processing module 308 can map a patient's vasculature that is within the view of the ultrasound emitter(s) 304. Based on the vasculature, the beamforming and/or other imaging techniques can focus on a best vessel of opportunity of the mapped vasculature and can calculate real-time blood pressure 314 and/or vessel dynamics 310.

Figure 5:
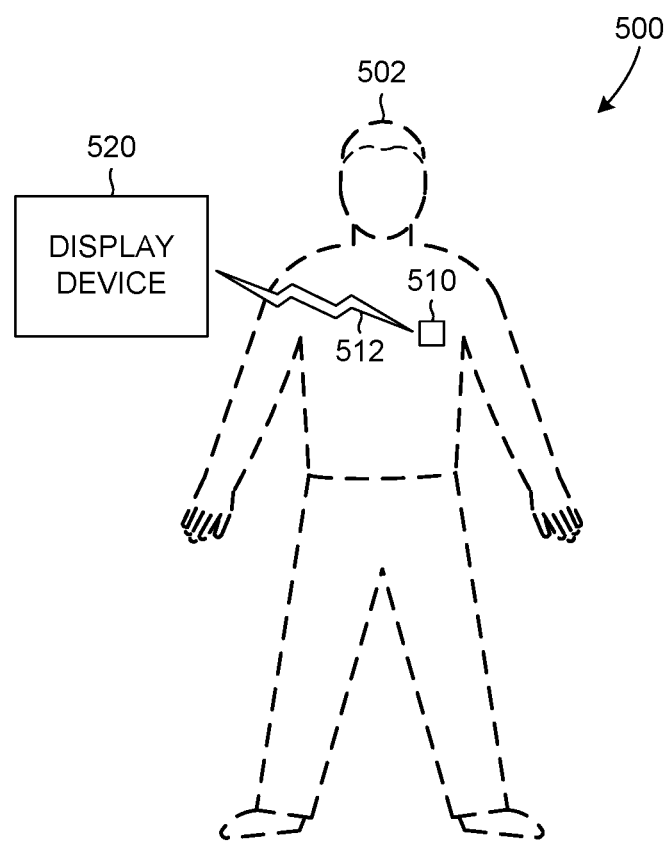
FIG. 5 is an example NIBP patch system.

FIG. 5 illustrates an example non-invasive blood pressure (NIBP) patch system 500 that includes an NIBP patch 510 that communicates 512 with a display device 520. The NIBP patch 510 can calculate and/or monitor a blood pressure of a patient 502 on which the NIBP patch 510 is placed on, and/or affixed. The NIBP patch 510 can include one or more emitters and sensors to radiate energy, such as ultrasound or light, into tissues of the patient 502 and to sense the energy reflected therefrom. The reflected energy can be received and processed to determine blood pressure and/or vessel dynamics of the patient 502. Additionally, the NIBP patch 510 can include other sensors, such as physiological, temperature and/or motion sensors, to monitor other physiological parameters and/or status of the patient 502 and/or status of the NIBP patch 510.

The display device 520 can receive, via communication 512, the collected data, such as blood pressure, vessel dynamics, physiological and/or NIBP patch 510 status data, for display. The display device 520 can include a visual display, such as a screen, and/or an audible display, such as a speaker, to present the received data from the NIBP patch 510. In addition to displaying the received data, the display device 520 can also display data received from other sources, such as other devices/system monitoring and/or treating the patient 502, to provide comprehensive display of patient 502 data. Additionally, the display device 520 can correlate the data displayed thereon to assist with monitoring and/or treating the patient 502.

Data received by the display 520 from the NIBP patch 510 can also be transmitted by the display 520, and/or NIBP patch 510, to another external user, device and/or system.

The display device 520 can receive data from the NIBP patch 510 continuously and/or in intervals. In an example, the display device 520 can interrogate the NIBP patch 510 to receive a response from the NIBP patch 510 that includes the data.

Communications 512 between the display device 520 and the NIBP patch 510 can include data transmissions and, optionally, power transmissions, such as via a near-field communication (NFC). In an example, the display device 520 can broadcast a power signal, such as a radio transmission, that can be received by the NIBP patch 510 to induce a current in the NIBP patch 510 that powers one or more functions/features of the NIBP patch 510. In response, the NIBP patch 510 can perform the one or more functions/features and/or transmit collected data from the NIBP patch 510 to the display device 520. This can allow the NIBP patch 510 to operate in a low/reduced-power mode when not receiving the power signal from the display device 520, operate when receiving the power signal from the display device 520 and/or transmit data in response to the power, or other, signal from the display device 520.

It will be appreciated that variants of the above-disclosed and other features and functions, or alternatives thereof, may be combined into many other different devices, systems and/or applications. Various presently unforeseen or unanticipated alternatives, modifications, variations, or improvements therein may be subsequently made by those skilled in the art which are also intended to be encompassed by the following claims.

The invention claimed is:

1. A non-invasive blood pressure (NIBP) monitoring system, comprising:
   a housing configured to be adhered to a patient;
   an emitter configured to emit ultrasound toward blood flowing through a vessel of the patient, the ultrasound emission comprising grating lobes separated by an angle;
   a receiver configured to detect a reflection of the ultrasound from the blood;
   a sensor configured to detect a temperature of the NIBP monitoring system;
   a transceiver configured to transmit data; and
   a processor configured to:
      determine a velocity at which the blood flows by analyzing the reflection of the ultrasound;
      determine a depth between the receiver and the vessel;
      determine, using triangulation with the angle and the depth, a pulse wave velocity (PWV) that corresponds to a rate at which a pulse travels through the vessel;
      in response to determining the velocity and determining the PWV, determine a blood pressure as a function of the velocity and the PWV;
      in response to determining that the temperature exceeds a threshold, cease the analyzing of the reflection and the determining of the blood pressure and disable the transceiver; and
      in response to determining that the temperature ceases to exceed the threshold, resume the analyzing of the reflection and the determining of the blood pressure and activate the transceiver.

2. The NIBP monitoring system of claim 1, further comprising:
   a battery configured to supply power to the emitter and the transceiver,
   wherein the disabling comprises disabling the emitter, the transceiver, and the battery when the temperature exceeds the threshold, and
   wherein the activating comprises activating the emitter, the transceiver, and the battery when the temperature ceases to exceed the temperature.

3. The NIBP monitoring system of claim 1, wherein the disabling comprises disabling the emitter, the transceiver, and the processor when the temperature exceeds the threshold, and
   wherein the activating comprises activating the emitter, the transceiver, and the processor when the temperature ceases to exceed the temperature.

4. The NIBP monitoring system of claim 1, wherein NIBP patch is affixed to the patient by an adhesive when the patient is in motion.

5. The NIBP monitoring system of claim 1, wherein the processor is further configured to:
   control the blood pressure to be determined when the NIBP monitoring system operates in a power mode in response to power received wirelessly from a computing device; and
   control the blood pressure to be determined when the NIBP monitoring system operates in a low-power mode in response to the power not being received wirelessly from the computing device.

6. The NIBP monitoring system of claim 1, wherein the determining the blood pressure is performed without calibration.

7. The NIBP monitoring system of claim 1, wherein the determining the PWV is performed by computing, without restriction of flow of the blood, the PWV.

8. The non-invasive blood pressure (NIBP) monitoring system of claim 1, wherein the processor is further configured to:
   operate the NIBP monitoring system in a low-power mode.

9. A system, comprising:
   an emitter configured to emit ultrasound, the ultrasound emission comprising grating lobes separated by an angle;
   a receiver configured to generate a signal by detecting a reflection of the ultrasound from blood in a vessel of a patient without restricting the vessel of the patient;
   a sensor configured to detect a temperature of a device that includes the emitter and the receiver;
   a transceiver configured to transmit data to a computing device; and
   a processor configured to:
      determine a velocity of the blood in the vessel;
      determine a depth between the receiver and the vessel;
      determine, using triangulation with the angle and the depth, a pulse wave velocity (PWV) for the vessel by using the signal to analyze movement of the blood through the vessel over an interval of time;
      in response to determining the velocity and determining the PWV, determine a blood pressure as a function of the velocity and the PWV;
      in response to the temperature exceeding a threshold, cease the analyzing of the reflection and the determining of the blood pressure and temporarily disable the transceiver, and
      in response to the temperature ceasing to exceed the threshold, resume the analyzing of the reflection and the determining of the blood pressure and activate the transceiver.

10. The system of claim 9, wherein the disabling comprises disabling the emitter and the transceiver when the temperature exceeds the threshold, and wherein the activating comprises activating the emitter and the transceiver when the temperature ceases to exceed the temperature.

11. The system of claim 9, further comprising:
a battery configured to supply power to the emitter and the transceiver,
wherein the disabling comprises disabling the emitter, the transceiver, and the battery when the temperature exceeds the threshold, and
wherein the activating comprises activating the emitter, the transceiver, and the battery when the temperature ceases to exceed the temperature.

12. The system of claim 9, wherein the processor is further configured to:
control the data to be transmitted in response to power received wirelessly from the computing device and a current induced in the device by the power; and
control the data being transmitted to cease in response to the power not being received wirelessly from the computing device.

13. The system of claim 9, further comprising:
a housing configured to be adhered to the patient; and
a patch that includes the housing, the emitter, the receiver, the sensor, the transceiver, and the processor.

14. The system of claim 9, wherein the data includes a notice indicating the blood pressure.

15. The system of claim 9, wherein the processor is further configured to determine a cardiac condition of the patient or vessel dynamics of the patient in response to the PWV being determined without restriction of flow of the blood.

16. The system of claim 9, further comprising:
an amplifier configured to amplify the signal; and
an analog-to-digital (ADC) configured to convert the signal,
wherein the data transmitted by the transceiver includes the signal that is amplified and converted.

17. A method comprising:
emitting, by an emitter of a device, ultrasound toward blood flowing through a vessel of a patient, the ultrasound emission comprising grating lobes separated by an angle;
detecting, by a receiver, a reflection of the ultrasound from the blood;
detecting, by a sensor, a temperature of the device;
transmitting, by a transceiver, data to a computing device; and
determining, by a processor, a velocity at which the blood flows by analyzing the reflection of the ultrasound;
determining a depth between the receiver and the vessel;
determining, by the processor and using triangulation with the angle and the depth, a pulse wave velocity (PWV) that corresponds to a rate at which a pulse travels through the vessel;
in response to determining the velocity and determining the PWV, determining, by the processor, a blood pressure as a function of the velocity and the PWV;
in response to determining that the temperature exceeds a threshold:
ceasing the analyzing of the reflection and the determining of the blood pressure, and
disabling the transceiver or the processor; and
in response to determining that the temperature ceases to exceed the threshold:
resuming the analyzing of the reflection and the determining of the blood pressure, and
activating the transceiver or the processor.

18. The method of claim 17, wherein the disabling comprises disabling the emitter and the transceiver when the temperature exceeds the threshold, and
wherein the activating comprises activating the emitter and the transceiver when the temperature ceases to exceed the temperature.

19. The method of claim 17, wherein the disabling comprises disabling the emitter, the transceiver, and the processor when the temperature exceeds the threshold, and
wherein the activating comprises activating the emitter, the transceiver, and the processor when the temperature ceases to exceed the temperature.

20. The method of claim 17, wherein the determining the PWV comprising determining the PWV without restriction of flow of the blood.

* * * * *